US010066335B2

(12) United States Patent
Arpino

(10) Patent No.: US 10,066,335 B2
(45) Date of Patent: Sep. 4, 2018

(54) DEVICE FOR SENSING THE ELECTRICAL CONDUCTIVITY OF A LIQUID, PARTICULARLY THAT OF THE WASHING BATH IN A WASHING MACHINE

(71) Applicant: BITRON S.p.A., Turin (IT)

(72) Inventor: Fabio Arpino, Milan (IT)

(73) Assignee: BITRON S.P.A., Turin (IT)

( * ) Notice: Subject to any disclaimer, the term of this patent is extended or adjusted under 35 U.S.C. 154(b) by 0 days.

(21) Appl. No.: 15/794,614

(22) Filed: Oct. 26, 2017

(65) Prior Publication Data
US 2018/0044838 A1 Feb. 15, 2018

Related U.S. Application Data

(63) Continuation of application No. PCT/IB2016/052345, filed on Apr. 26, 2016.

(30) Foreign Application Priority Data

Apr. 27, 2015 (IT) .......................... 102015000013209

(51) Int. Cl.
D06F 39/00 (2006.01)
D06F 39/08 (2006.01)
(Continued)

(52) U.S. Cl.
CPC ............ D06F 39/004 (2013.01); D06F 39/02 (2013.01); D06F 39/081 (2013.01);
(Continued)

(58) Field of Classification Search
CPC ........ G01F 23/241; D06F 39/02; G01R 27/22
See application file for complete search history.

(56) References Cited

U.S. PATENT DOCUMENTS 4,118,663 A 10/1978 Barben, II
5,025,220 A * 6/1991 Colvin .................. G01N 27/07
324/444

(Continued)

FOREIGN PATENT DOCUMENTS

DE 32 11 385 A1 8/1983
EP 2 166 143 A1 3/2010

OTHER PUBLICATIONS

International Search Report for PCT/IB2016/052345 dated Aug. 5, 2016.

Primary Examiner — Giovanni Astacio-Oquendo
Assistant Examiner — Alvaro Fortich
(74) Attorney, Agent, or Firm — Sughrue Mion, PLLC

(57) ABSTRACT

A device for sensing the electrical conductivity of a liquid, particularly that of the washing bath in a washing machine, including an electrically insulating supporting casing through which first and second electrodes intended to contact the washing bath extend to the outside, electrical power supply and signal acquisition and processing circuit devices housed at least in part in the supporting casing and coupled to the electrodes, and signal coupling and galvanic isolation devices, interposed between these circuit devices and the electrodes and also housed in the casing, and including at least a first and a second capacitor, each of which is interconnected in series between one of the electrodes and a corresponding terminal of the circuit.

10 Claims, 4 Drawing Sheets

(51) Int. Cl.
  *G01N 27/07* (2006.01)
  *G01R 27/22* (2006.01)
  *D06F 39/02* (2006.01)
  *G01N 27/06* (2006.01)
  *G01F 23/24* (2006.01)
  *H01H 37/76* (2006.01)
  *H01H 37/04* (2006.01)

(52) U.S. Cl.
  CPC ........... *G01F 23/241* (2013.01); *G01N 27/06* (2013.01); *G01N 27/07* (2013.01); *G01R 27/22* (2013.01); *H01H 2037/046* (2013.01); *H01H 2037/762* (2013.01)

(56) References Cited

U.S. PATENT DOCUMENTS

| | | | |
|---|---|---|---|
| 5,315,847 A | 5/1994 | Takeda et al. | |
| 5,519,323 A | 5/1996 | Kordas et al. | |
| 5,767,682 A * | 6/1998 | Sekimoto | G01N 27/023 |
| | | | 324/204 |
| 6,573,734 B2 * | 6/2003 | He | G01N 27/07 |
| | | | 324/696 |
| 2014/0152332 A1 | 6/2014 | Platte et al. | |

* cited by examiner

DEVICE FOR SENSING THE ELECTRICAL CONDUCTIVITY OF A LIQUID, PARTICULARLY THAT OF THE WASHING BATH IN A WASHING MACHINE

CROSS REFERENCE TO RELATED APPLICATIONS

This application is a Bypass Continuation of International Application No. PCT/IB2016/052345 filed Apr. 26, 2016, claiming priority based on Italian Patent Application No. 102015000013209 filed Apr. 27, 2015, the contents of all of which are incorporated herein by reference in their entirety.

BACKGROUND OF THE INVENTION

Field of the Invention

The present text concerns a device for sensing the electrical conductivity of a liquid, particularly that of the washing bath in a washing machine such as a dishwasher or a clothes washing machine.

More specifically, the invention relates to a sensing device of the type comprising
- an electrically insulating supporting casing, through which first and second electrodes, intended to contact the liquid, extend to the outside,
- electrical power supply and signal acquisition and processing circuit means, housed at least in part in the supporting casing and coupled to said electrodes, and
- signal coupling and galvanic isolation means, interposed between said circuit means and the electrodes, and likewise housed in said casing.

BACKGROUND

A sensing device of this type is known from the prior U.S. Pat. No. 5,315,847A.

In this electrical conductivity sensing device according to the prior art, the signal coupling and galvanic isolation means comprise a transformer whose primary winding is connected between the electrodes, and whose secondary winding is connected to the signal acquisition and processing circuit means.

This solution is cumbersome and costly.

One object of the present invention is therefore to provide a device for sensing the electrical conductivity of a liquid, particularly for the washing bath in a washing machine, which enables the aforementioned drawbacks of the prior art devices to be overcome.

SUMMARY OF THE INVENTION

This and other objects are achieved according to the invention with a sensing device of the type defined initially, characterized in that the aforesaid galvanic isolation and coupling means comprise at least a first and a second capacitor, each of which is interconnected in series between one of said electrodes and a corresponding terminal of the aforesaid circuit means.

Conveniently, one or more capacitors, having a total capacitance in the range from 0.5 to 2.5 nF (for each electrode), are interposed between each of the electrodes and the corresponding terminal of the circuit means.

The aforesaid circuit means may comprise means for generating pulses, particularly square-wave pulses, of predetermined frequency, coupled to one of the aforesaid electrodes, and envelope detector means, coupled to the other or second electrode.

In one embodiment, the pulse generator means are provided by using a microprocessor, and the output of the envelope detector means is coupled to an input of this microprocessor.

The electrical conductivity sensing device according to the present invention can be made in integrated form, in a single supporting casing, with a device for detecting the turbidity of the washing bath, comprising a photoemitter and a photodetector facing one another.

In this case, the circuit means for the electrical power supply and the acquisition and processing of signals may conveniently comprise a microprocessor, also designed to modify the operating characteristic or response of the turbidity detector device, in such a way that it conforms to a predetermined characteristic.

The electrical conductivity sensing device according to the present invention may also be produced with at least one further electrode, for the additional provision of signals indicative of the height or level of the liquid in the container or vessel containing it.

BRIEF DESCRIPTION OF THE DRAWINGS

Further characteristics and advantages of the invention will be apparent from the following detailed description which is given purely by way of non-limiting example, with reference to the attached drawings, in which.

DETAILED DESCRIPTION OF THE INVENTION

Figure 1:
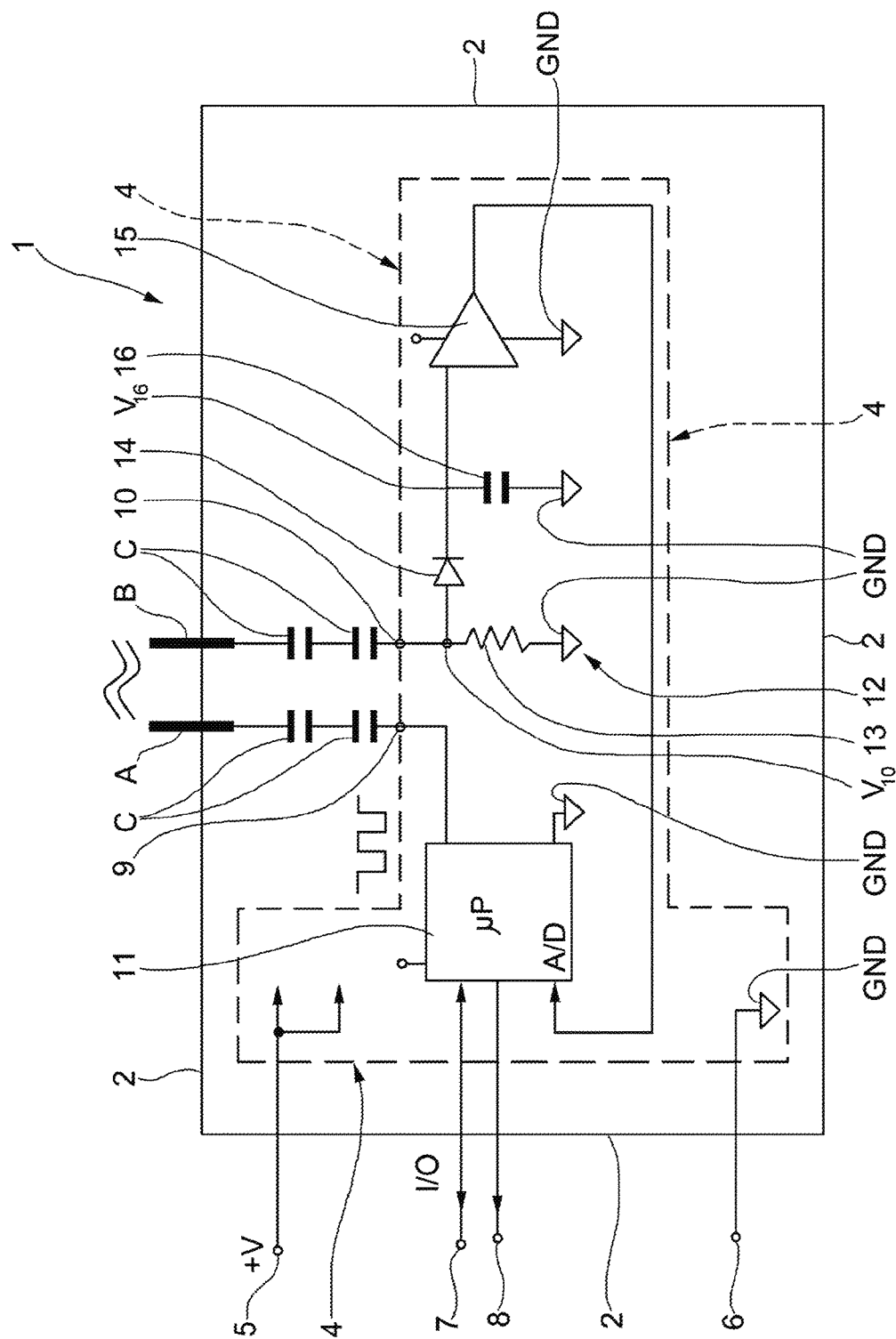
FIG. 1 is a circuit diagram of an electrical conductivity sensing device according to the present invention.

In FIG. 1, the number 1 indicates the whole of a device for sensing the electrical conductivity of the washing bath in a washing machine (not shown).

This sensor 1 comprises a supporting casing 2, of electrically isolating material, through which a first and a second electrode A and B, intended to contact the washing bath, extend to the outside.

The electrodes A and B are made of stainless steel, for example.

Electrical power supply and signal acquisition and processing circuit devices, indicated as a whole by 4 in FIG. 1, are housed in the supporting casing 2.

In the illustrated embodiment, these circuits 4 have four terminals 5, 6, 7 and 8 which are accessible from the outside.

The terminals 5 and 6 are intended to be connected to the terminals of a continuous voltage supply source.

In particular, the terminal 5 in the casing 2 is connected, in a manner which is not shown, to power supply terminals of various devices included in the circuits 4, while the terminal 6 is connected to a conductor R which, in operation, is at a reference potential.

The terminals 7 and 8 are an input/output terminal and an output terminal, respectively.

Within the isolating supporting casing 2, the circuits 4 have two terminals indicated by 9 and 10, which are coupled, in a manner described more fully below, to the electrodes A and B respectively.

In the illustrated embodiment, the circuits 4 comprise a microprocessor 11, of a known type, connected to the terminals 7, 8 and 9.

In operation, the microprocessor 11 sends a train of pulses, particularly square-wave pulses, of predetermined frequency (although the frequency is not critical), to the electrode A through the terminal 9.

The circuits 4 further comprise a peak or envelope detector, indicated as a whole by 12. This detector comprises, in particular, a resistor 13, connected between the terminal 10 and the conductor R, a diode 14 having its anode connected to the terminal 10 and its cathode connected to an input of an amplifier 15, and a capacitor 16 connected between the cathode of the diode 14 and the conductor R.

The output of the amplifier 15 is connected to an input of the microprocessor 11, leading to an internal analogue/digital converter.

Signal coupling and galvanic isolation devices, which in the illustrated embodiment consist of two capacitors C connected to one another in series, are interposed between each of the terminals 9 and 10 and the associated electrode A and B.

The two capacitors C connected in series to each electrode preferably both have the same capacitance, in the range from 1 to 5 nF, giving a total capacitance per electrode in the range from 0.5 to 2.5 nF.

This total capacitance is optimal, for the reasons given above.

Figure 2:
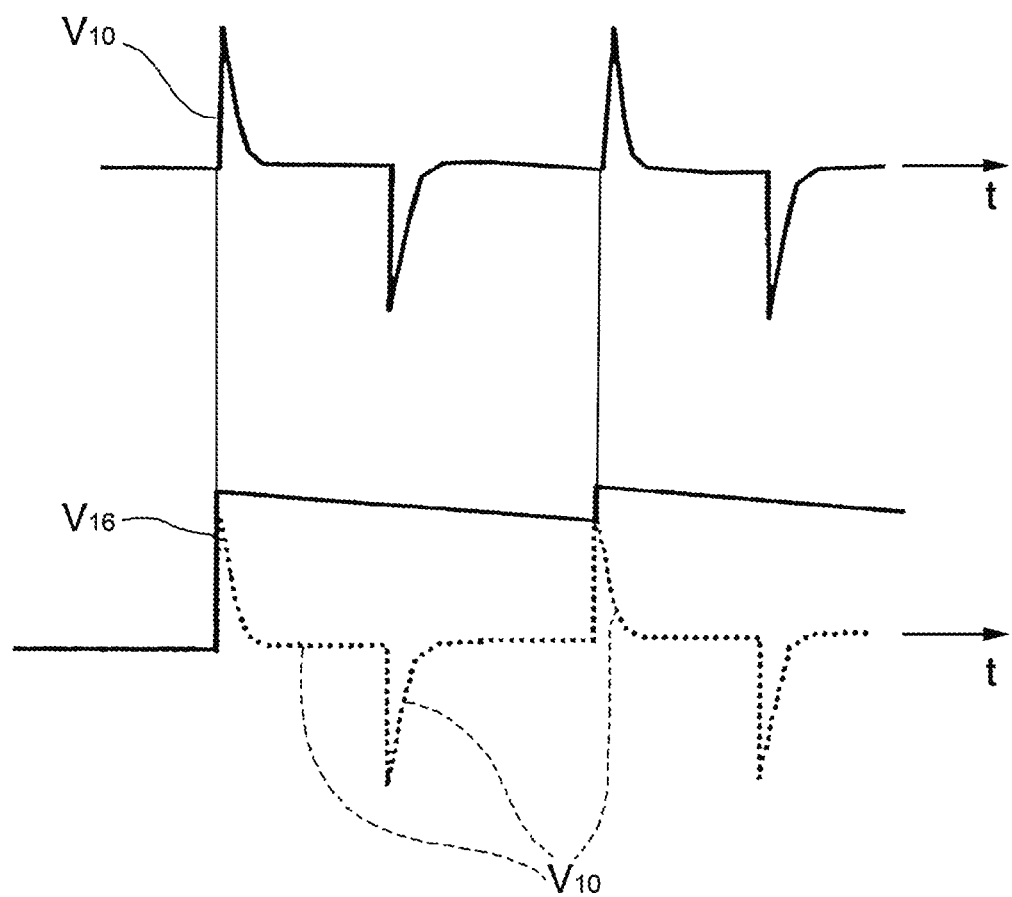
FIG. 2 is a set of two timing charts showing the variation of two signals generated in the electrical conductivity sensing device according to FIG. 1.

In operation, as a result of the application of a train of pulses by the microprocessor 11 to the terminal 9, and therefore to the electrode A, a pulsed voltage $V_{10}$ appears in operation between the electrodes A and B at the terminal 10 as a result of the conductivity of the washing water, the variation of this voltage as a function of the time t shown on the horizontal axis being qualitatively illustrated in the upper graph of FIG. 2.

In a corresponding way, a voltage $V_{16}$ is developed between the cathode of the diode 14 and the conductor R, that is to say at the terminals of the capacitor 16, the variation of this voltage as a function of the time t being qualitatively illustrated in the lower diagram of FIG. 2: as the conductivity of the washing bath between the electrodes A and B increases, the mean value of the voltage $V_{16}$ also increases.

After being amplified by the amplifier 15, the voltage $V_{16}$ reaches the microprocessor 11, which then provides corresponding output data at the terminal 8.

As mentioned previously, a total signal coupling and galvanic isolation capacitance, advantageously in the range from 1 to 5 nF, is interposed between each of the terminals 9 and 10 of the circuits 4 and the associated electrode A and B. A capacitance selected in this optimal range facilitates the discrimination of the pulses of the voltage $V_{10}$ from any pulsed interference, while it enables the strength of the current injected into the washing bath to be kept at modest levels. The capacitors used to provide this capacitance can therefore be of small size and low cost.

Figure 3:
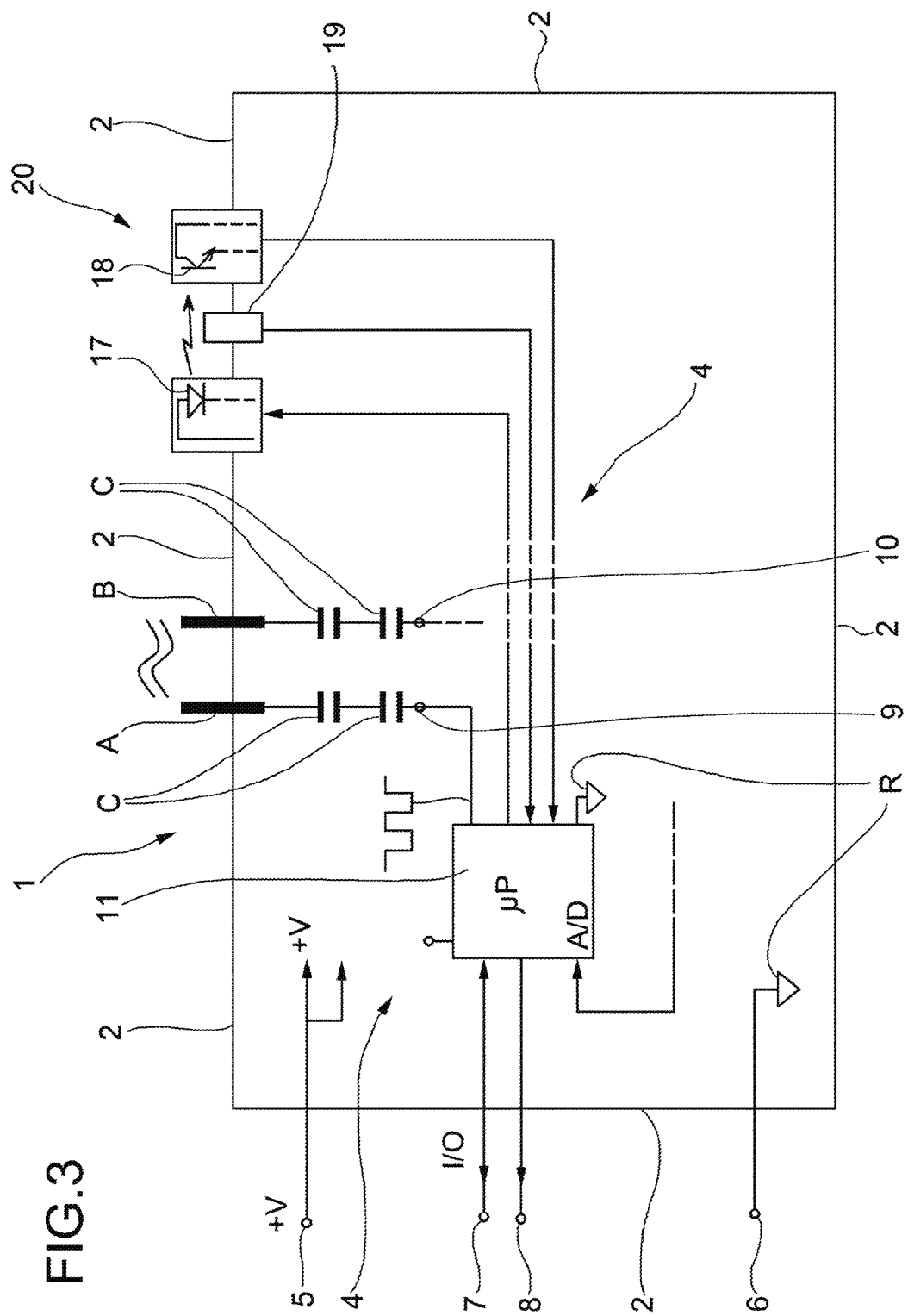
FIG. 3 is a diagram of an electrical conductivity sensing device integrated with a device for detecting the turbidity of the washing bath.

FIG. 3 shows a variant embodiment in which the electrical conductivity sensor 1 is made to be integrated, in the same supporting casing 2, with a device 20 for detecting the turbidity of the washing bath.

In FIG. 3, parts and elements described previously have again been given the same alphabetical and numeric references as those used previously. For simplicity of illustration, the part relating to the envelope detector 12 has been omitted from the diagram of FIG. 3.

In the variant according to FIG. 3, the combined electrical conductivity and washing bath turbidity sensor further comprises a photoemitter 17 and a photodetector 18, placed facing one another in respectively at least partially transparent portions of casing, in an arrangement such that a portion of the washing bath extends, in operation, on the path of the radiation between the photoemitter and the photodetector.

In a known way, the turbidity detector device 20 can be associated with a temperature sensor 21 for detecting the temperature of the washing bath.

In the illustrated embodiment, the photoemitter 17, the photodetector 18 and the temperature sensor 19 are all connected to the microprocessor 11. The microprocessor is, in particular, conveniently designed to modify the operating characteristic or response of the turbidity sensing device 20, in such a way that it corresponds to a predetermined nominal characteristic.

For this purpose, the microprocessor 11 may comprise internal or external memory means adapted to store data representative of correction values which, when applied in operation to the effective instantaneous values of the signal output from the photodetector 18, can be used to find correct values of this signal, corresponding to the desired nominal transduction characteristic.

Figure 4:
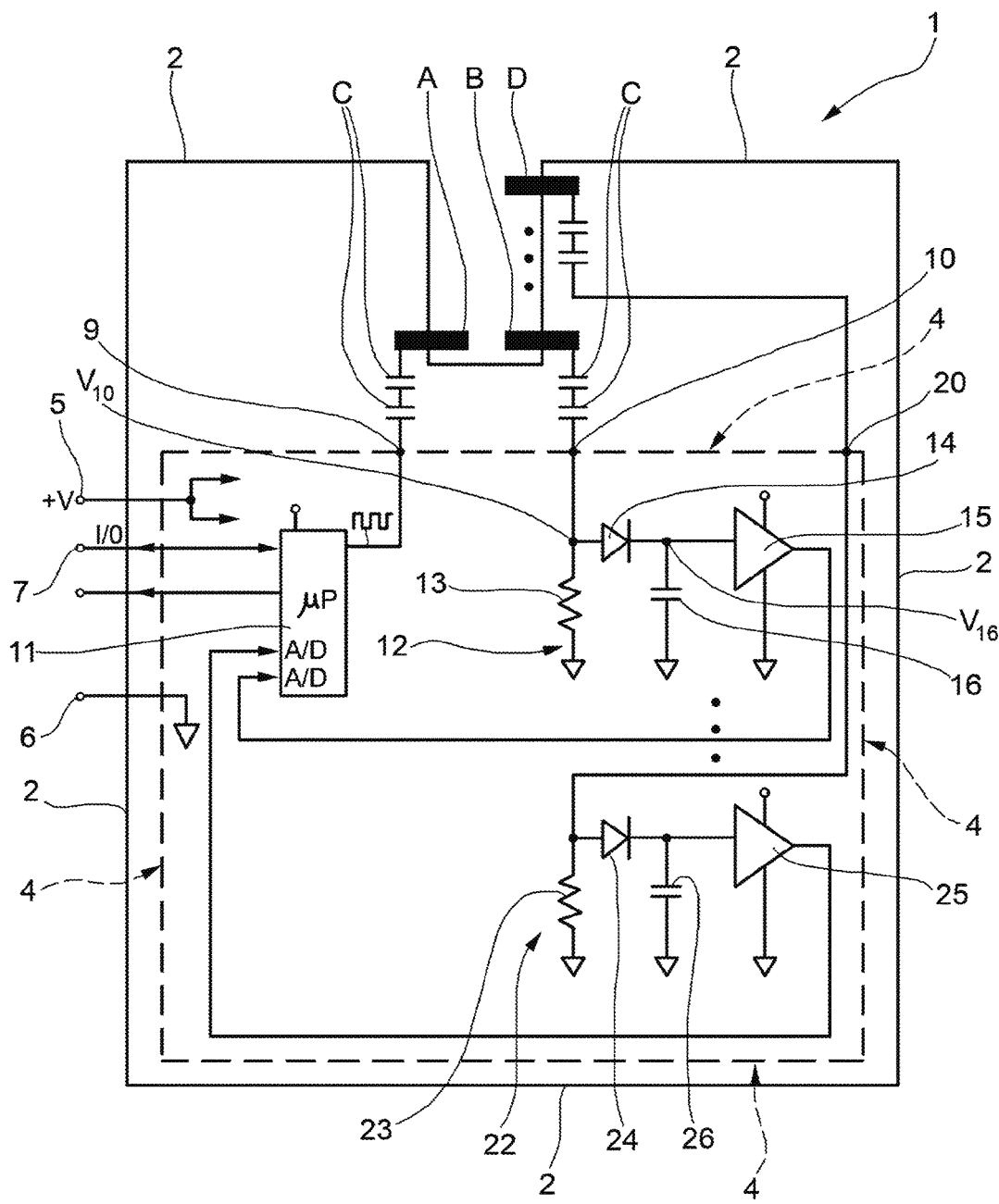
FIG. 4 is a diagram of an electrical conductivity sensing device adapted for the additional provision of signals indicative of the height or level of the liquid in the container or vessel containing it.

FIG. 4 shows another variant embodiment of the conductivity sensing device according to the invention. In this figure also, parts and elements described previously have again been given the alphabetical and numeric references used previously.

In the variant according to FIG. 4, at least one further electrode D extends through the supporting casing 2, in such a position that, in use, it contacts the bath in the washing chamber at a different level, for example a higher level, than the level of the second electrode B.

The electrode D is coupled to a further terminal 20 of the circuits 4, which is connected to a further peak or envelope detector 22, similar to the peak detector 12 described above, comprising a resistor 23, a diode 24, a capacitor 26 and an amplifier 25.

The output of the detector 22 is connected to a further input A/D of the microprocessor 11. The latter is designed to supply signals or data indicative of the level of the washing bath, on the basis of the signals available during operation on the electrode D (or on the resistor 23) and on the electrode B (or on the resistor 13).

By adding any necessary further electrodes placed at various levels, and associated detector circuits, the resolution of the measurement of the washing bath level can be improved.

Finally, an electrical conductivity sensing device according to the invention can be used to detect the presence of washing bath liquid in a collecting vessel, such as a tray or the like, placed under the washing chamber of a washing machine, to signal a condition of leakage or flooding.

Naturally, the principle of the invention remaining the same, the forms of embodiment and the details of construction may be varied widely with respect to those described and illustrated, which have been given purely by way of non-limiting example, without thereby departing from the scope of the invention as defined in the attached claims.

The invention claimed is:

1. A sensing device for sensing the electrical conductivity of a liquid, comprising:
   an electrically insulating supporting casing through which first and second electrodes intended to contact said liquid extend to an outside;
   an electrical power supply and a signal acquisition and processing circuit means housed at least in part in the electrically insulating supporting casing and coupled to said first and second electrodes; and
   a signal coupling and galvanic isolation means, interposed between said processing circuit means and said first and second electrodes and likewise housed in said electrically insulating supporting casing,
   wherein said signal coupling and galvanic isolation means comprise at least a first and a second capacitor, each of which is interconnected in series between one of said first and second electrodes and a corresponding terminal of said processing circuit means.

2. The sensing device according to claim 1, wherein between each of said first and second electrodes and the corresponding terminal of the processing circuit means there are interposed one or more capacitors, having a total capacitance in a range from 0.5 to 2.5 nF.

3. The sensing device according to claim 1, wherein said processing circuit means comprise a pulse generator means, particularly for generating square-wave pulses, having a predetermined frequency, connected to the first electrode.

4. The sensing device according to claim 3, wherein said processing circuit means comprise an envelope detector means coupled to the second electrode.

5. The sensing device according to claim 3, wherein the pulse generator means are formed by a microprocessor, and wherein an output of an envelope detector means is coupled to an input of said microprocessor.

6. The sensing device according to claim 5, the sensing device integrated with a device for detecting a turbidity of a washing bath, of the type comprising a photoemitter and a photodetector optically coupled to one another.

7. The sensing device according to claim 1, wherein
   at least one further electrode extends through said electrically insulating supporting casing so as to contact a washing bath at a different level from said second electrode,
   said at least one further electrode being coupled, through a further first and a further second capacitor interconnected in series, to said electrical power supply said and acquisition and processing circuit means, which are designed to supply, on the basis of signals available during an operation on the second electrode and on said at least one further electrode, signals or data indicative of the level of said washing bath.

8. The sensing device according to claim 7, wherein said processing circuit means comprises at least one further envelope detector means coupled to said at least one further electrode.

9. A washing machine comprising the sensing device according to claim 1.

10. A use of the sensing device according to claim 1 for detecting a presence of water in a collecting vessel such as a tray placed under a washing chamber of a washing machine, to signal a condition of a leakage or flooding.

* * * * *